US007603907B2

United States Patent
Reiter et al.

(10) Patent No.: US 7,603,907 B2
(45) Date of Patent: Oct. 20, 2009

(54) MEMBRANE UNIT, HOUSING OF A PRESSURE MEASURING UNIT AND PRESSURE MEASURING UNIT

(75) Inventors: Reinhold Reiter, Crema (IT); Marco Caronna, Modena (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 11/667,944

(22) PCT Filed: Nov. 10, 2005

(86) PCT No.: PCT/EP2005/012042

§ 371 (c)(1),
(2), (4) Date: May 17, 2007

(87) PCT Pub. No.: WO2006/053673

PCT Pub. Date: May 26, 2006

(65) Prior Publication Data

US 2007/0295093 A1    Dec. 27, 2007

(30) Foreign Application Priority Data

Nov. 17, 2004 (EP) ................................ 04425855

(51) Int. Cl.
*G01L 7/00* (2006.01)
(52) U.S. Cl. .......................................... 73/715; 73/706
(58) Field of Classification Search .................. 73/715, 73/706, 730
See application file for complete search history.

(56) References Cited

U.S. PATENT DOCUMENTS

| 5,614,677 | A  | 3/1997  | Wamsiedler et al. |
| 6,725,726 | B1 | 4/2004  | Adolfs et al. |
| 2003/0115965 | A1 | 6/2003  | Mittelstein et al. |
| 2003/0200812 | A1 | 10/2003 | Kuhn et al. |
| 2004/0050168 | A1 | 3/2004  | Uberreiter |

FOREIGN PATENT DOCUMENTS

WO    WO 99/37983    7/1999

*Primary Examiner*—Andre J Allen
(74) *Attorney, Agent, or Firm*—Jacobson Holman PLLC

(57) ABSTRACT

A membrane unit configured for use in a housing of a pressure measuring unit, preferably for measuring pressure in an extracorporal blood circuit, has a flexible membrane and a fixing ring which is integral with the membrane so that the membrane and the fixing ring form a one-piece element. The fixing ring has a lower flexibility than the membrane, and has fixing elements for fixing the fixing ring to the pressure measuring housing.

20 Claims, 3 Drawing Sheets

MEMBRANE UNIT, HOUSING OF A PRESSURE MEASURING UNIT AND PRESSURE MEASURING UNIT

CROSS-REFERENCE TO RELATED APPLICATION

This is a national stage of PCT/EP05/012042 filed Nov. 10, 2005 and published in English.

BACKGROUND OF THE INVENTION

1. Field of Invention

The present invention refers to a membrane unit adapted for use in a housing of a pressure measuring unit which unit is preferably adapted to measure the pressure in an extra-corporeal blood circuit. Such pressure measuring units are usually referred to as "dome" or "pressure dome". These units comprise a membrane forming one surface of a pressure measuring chamber which membrane in use is in contact with a fluid and with a pressure transducer for converting pressures and pressure changes of the fluid into electrical signals.

2. Description of the Prior Art

A pressure measuring unit comprising a membrane and a housing is known from U.S. Pat. No. 5,614,677. The pressure measuring unit disclosed in this document comprises a housing comprising a pressure measuring chamber which is in fluid communication with an inlet and outlet of the housing. One surface of the pressure measuring chamber is formed by a membrane which is fixed to the housing by means of a tension ring inserted in a groove on the upper surface of the housing. The tension ring is fixed in its position by aid of a guide of the transducer which is abutting the upper surface of the housing.

Prior art document WO99/37983 also discloses a pressure measuring unit comprising a housing with a pressure measuring chamber one surface of which is formed by a membrane. The membrane comprises a circumferentially extending bead which is located on the side of the membrane facing the measuring chamber and which is pressed into a groove of the housing. A similar arrangement is known from U.S. patent application US 2004/0050168 A1.

The pressure measuring units described in the prior art are disadvantageous as the mounting of the membrane to the housing is cumbersome or has to be established by the membrane itself which is made of soft material.

SUMMARY OF THE INVENTION

Accordingly, it is the object of the present invention to provide a membrane which can easily be fixed in a pressure measuring housing and at the same time exhibits good pressure transmitting and sealing properties.

This object is solved by a membrane unit as described herein. According to the invention a membrane unit is provided adapted to be inserted into a housing of a pressure measuring unit preferably used for measuring pressure in an extra-corporeal blood circuit which membrane unit comprises a flexible membrane and a fixing ring which is integral with the membrane so that the membrane and the fixing ring form a one-piece element, wherein the fixing ring has a lower flexibility than the membrane and wherein the fixing ring comprises fixing elements for fixing the fixing ring to the housing. Accordingly, the membrane is part of a one-piece element composed of the membrane and a fixing ring having a lower flexibility than the membrane. The invention ensures that the membrane is fixed reliably in the housing and thus reveals a good pressure transmitting property to a transducer facing the membrane on the other side than the fluid. Further a good sealing property of the membrane is obtained. A further advantage of the membrane unit according to the invention is that it can be easily mounted into the housing by engaging the fixing elements of the ring with the housing.

The fixing ring as well as the membrane can be connected to each other by means of a suitable connection technique for example by means of glueing or welding.

Alternatively, the fixing ring and the membrane can form a joint element which is manufactured in a common process of manufacture. One example of such a process is two-component injection moulding. Accordingly, the membrane unit can be manufactured as one part or can also be manufactured as two elements which are linked to each other in a second step.

In a further embodiment of the invention the fixing elements of the fixing ring are formed as at least one projection, groove or thread. Alternative fixing elements are also conceivable.

The fixing elements of the fixing ring are located in a further embodiment of the invention at the outside portion of the fixing ring. Further the fixing ring may comprise a U-shaped portion and the fixing elements are located at one or both facing sides of the legs of the U-shaped portion.

The fixing ring may be arranged in a standing upright position on the membrane, preferably on the circumferential portion of the membrane. Preferably the ring extends perpendicularly relative to the membrane.

Furthermore, the circumferential portion of the membrane may have a larger thickness than the central portion of the membrane to improve the sealing properties.

In a further embodiment of the invention the membrane has a circumferential extending sealing lip for sealing the contact surface between the membrane and the housing. The sealing lip is fixed in the correct position by means of the fixing ring which itself is fixed at the housing.

In a further embodiment the sealing lip, in particular together with the possible larger thickness portion in the circumferential portion of the membrane, extends into a first direction perpendicular relative to the planar area defined by the central portion of the membrane whereas the ring extends relative to this area into the opposite direction of said first direction. In this embodiment, during use the fluid whose pressure is to be determined contacts the central portion of the membrane from the side of the first direction whereas the pressure transducer contacts the membrane from the opposite site.

In another embodiment of the invention the membrane has a groove on the surface facing the fixing ring for receiving a portion of the fixing ring.

The contact surface between the membrane and the fixing ring may be provided with one or more projections extending from one of the membrane or the fixing ring which engage with a groove in the other of the membrane and the fixing ring. The contact surface for example can be formed by a groove in the surface of the membrane facing the fixing ring with the fixing ring being accommodated in this groove with its portion abutting the membrane.

In a further embodiment of the invention the shape of the sealing lip of the membrane equals the shape of the contact surface between the membrane and the fixing ring.

The present invention further refers to a housing of a pressure measuring unit which housing is adapted to receive a membrane unit, the housing comprising an inlet and an outlet for a fluid, the pressure of which is to be measured as well as a pressure measuring chamber being in fluid communication with the inlet and the outlet, wherein the pressure measuring chamber has an opening which is to be closed by a membrane which is to be inserted into the housing, wherein the housing further comprises fixing elements for fixing a membrane unit, preferably a membrane unit as described herein, to the housing wherein the fixing elements are located at one or more projections extending around said opening of the pressure measuring chamber.

The projection may extend perpendicularly relative to that surface of the pressure measuring chamber which is formed by a membrane, i.e. perpendicularly relative to the opening of the pressure measuring chamber which is to be closed by the membrane.

The projection may extend circumferentially around the longitudinal axis of the pressure measuring chamber which axis is perpendicular to said opening of the pressure measuring chamber. In a preferred embodiment the projection is located concentrically with the longitudinal axis of the pressure measuring chamber.

The fixing elements of the projection of the housing may be formed as groove, jut or thread.

In a further embodiment of the invention the fixing elements are located on that side of the projection which is oriented to said opening of the pressure measuring chamber. The fixing elements may extend perpendicularly to the projection.

The invention is further directed to a pressure measuring unit comprising a membrane unit and a housing as described herein, wherein the fixing elements of the membrane unit engage with the fixing elements of the housing and wherein the membrane of the membrane unit forms one surface of the pressure measuring chamber of the housing.

BRIEF DESCRIPTION OF THE DRAWINGS

Further details and advantages of the invention become apparent from an embodiment which is now described as an example by aid of the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
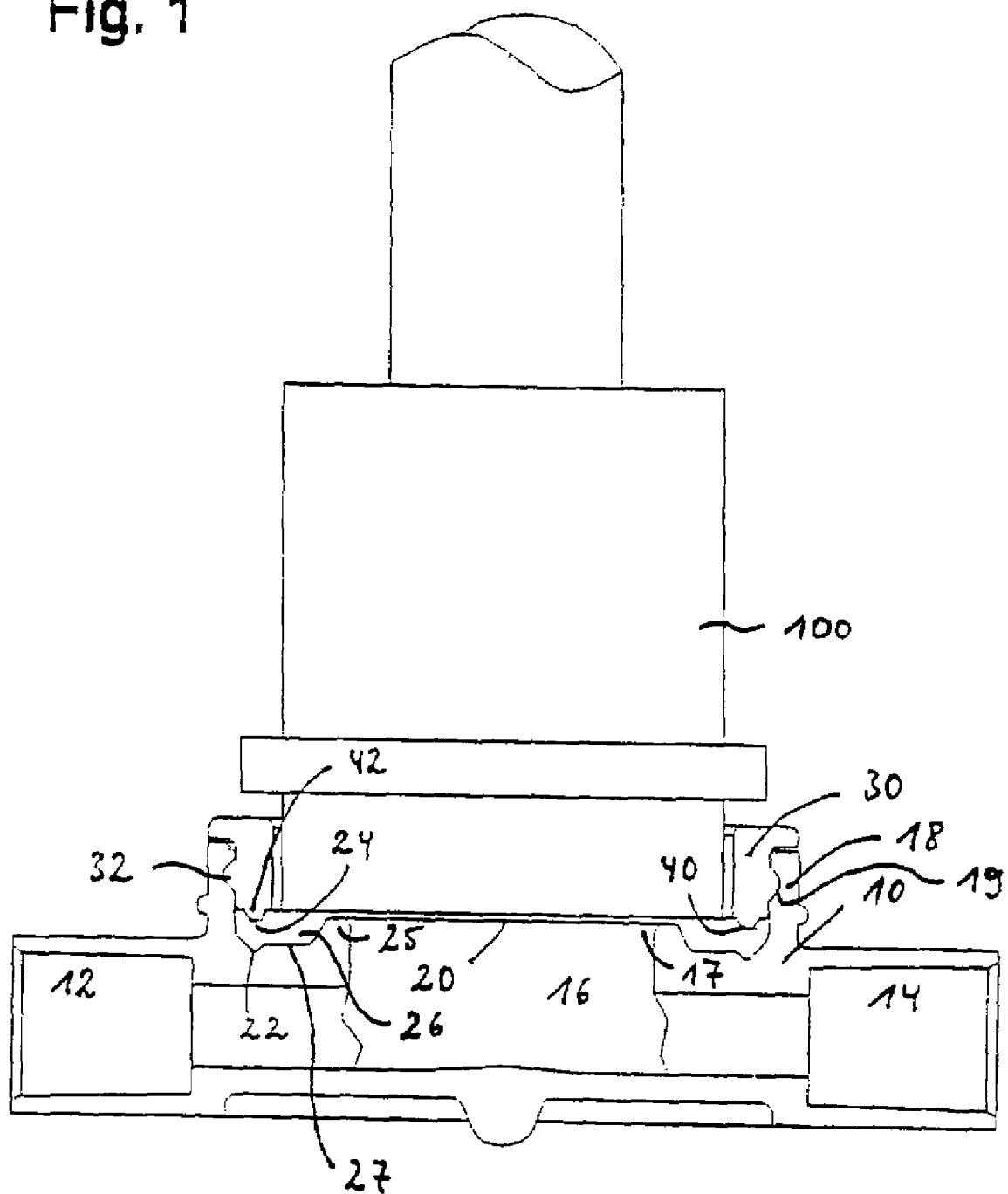
FIG. 1 shows the pressure measuring unit according to the invention with a pressure transducer inserted therein.

FIG. 1 shows the housing 10 comprising an inlet 12 and an outlet 14 for connection to an extra-corporeal blood circuit of a dialysis apparatus. Between the inlet 12 and the outlet 14 is located the pressure measuring chamber 16 which is in fluid communication with the inlet 12 and the outlet 14. In this embodiment the pressure chamber 16 has a circular cross section when viewed from the top. The pressure measuring chamber 16 is terminated at the top by the lower surface of a circular membrane 20 which closes the upper opening 17 of the pressure measuring chamber 16. At the edge of the membrane 20 there is a sealing lip 22 at the lower surface of the membrane 20 facing toward the housing 10 and a groove 24 on the upper surface of the membrane 20 facing a fixing ring 30. The interior walls of the pressure measuring chamber 16 below the membrane 20 may have any shape suitable for the required purpose (e.g. rounded edges for blood compatibility, not shown in detail).

The membrane 20 and the fixing ring 30 form a one-piece element which is connected after manufacture of both parts or which is manufactured in a single process, for example by injection moulding.

The fixing ring 30 is made from a rigid material for guaranteeing the position of the soft sealing membrane 20 after assembling. The membrane 20 is made from elastic flexible material (for example thermoplastic elastomer, rubber) for sealing purposes as well as for transmitting the pressure/pressure changes to the transducer 100 abutting the upper surface of the membrane 20.

The membrane 20 and the fixing ring 30 are in permanent contact with each other and the contact surface 40 between both parts is not flat for providing more surface for adhesion between the rigid material of the fixing ring 30 and the soft material of the membrane 20. In the present embodiment the contact surface 40 comprises a projection 42 of the fixing ring 30 which engages with a groove 24 on the upper surface of the membrane 20 facing the fixing ring 30.

As further shown in FIG. 1 the fixing ring 30 at its outer surface comprises a radial projection 32 which is inserted into a corresponding groove 19 on the inside of a cylindrical projection 18 of the housing 10. The projection 18 extends perpendicularly to and circumferentially around the membrane 20. At its inner surface the projection 18 comprises the circumferentially extending groove 19 in which as mentioned above the also circumferentially extending projection 32 of the fixing ring 30 is inserted. The projection 18 and the fixing ring 30 are arranged vertically, i.e. perpendicularly to the membrane 20.

The membrane unit consisting of membrane 20 and fixing ring 30 can easily be inserted into the housing 10. Due to the presence of a rigid material in form of the fixing ring 30 the desired position of the fixing ring 30 and of the membrane 20 is reliably established so that a good sealing property as well as a good pressure transmitting property of the membrane 20 are obtained. The membrane unit is easily connected to the housing 10 by pushing the membrane unit from the top until the projection 32 snaps into the groove 19. As both the fixing ring 30 and the projection 18 are made of sufficiently rigid materials a firm connection is achieved. At the same time the membrane 20 touches the rim 25 of an opening 17 in the housing 10 that is to be closed by the membrane 20. Using appropriate sizes this contact can be used to apply a certain amount of tension to the membrane 20 upon fixing the ring 30 to the housing 10. This tension may be advantageous for the pressure transmitting properties for fluid pressures both below and above ambient pressure.

As the circumferential portion of the membrane 20 comprises a larger thickness portion 26 that is positioned in a groove 27 surrounding the rim 25 of the housing 10 the membrane 20 is well sealed by this circumferential portion against the housing 10. The sealing is further supported by the sealing lip 22 that is pressed by the fixing ring 30 into a complementary structure in the groove 27.

As shown in FIG. 1 the fixing ring 30 is joined perpendicularly to the circumferential portion of the membrane 20.

In the shown embodiment the two parts are joined in a direction being opposite to the direction the larger thickness portion 26 extends relative to the planar area defined by the central portion of the membrane 20.

Figure 2:
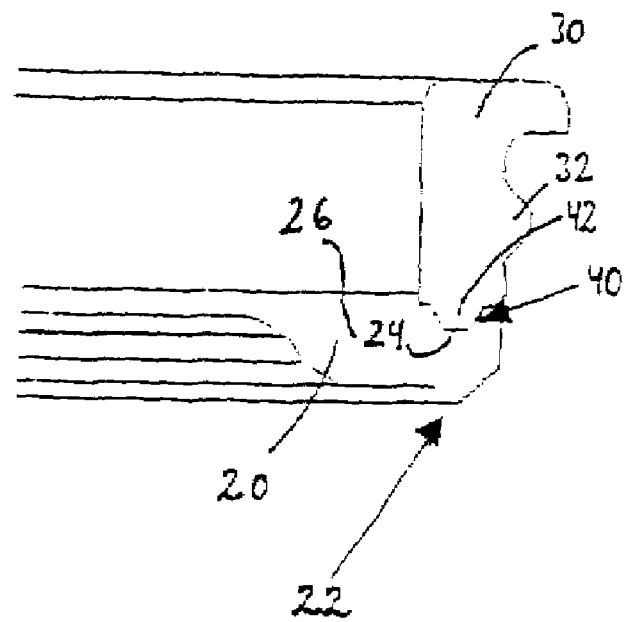
FIG. 2.
Figure 3:
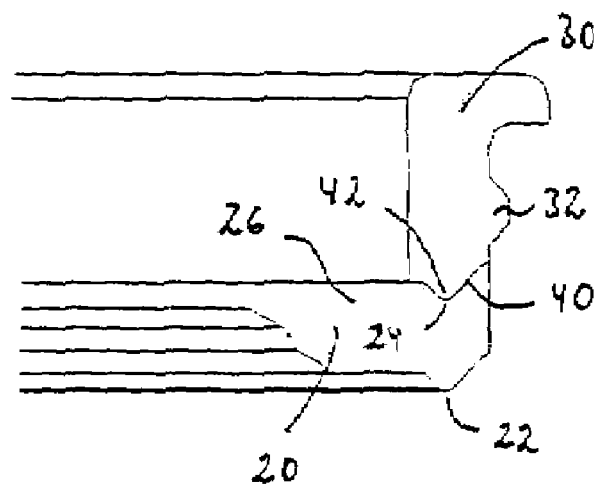
FIG. 3 show in detail the fixing ring and the membrane in different embodiments and FIG. 4 shows the fixing ring and the membrane after and before assembly according to FIG. 3.

FIGS. 2 and 3 show two different embodiments of the invention in which the contact surface 40 between the membrane 20 and the fixing ring 30 differs. According to FIG. 2 the contact surface 40 differs in its shape from the shape of the sealing lip 22 and in the embodiment of FIG. 3 the contact surface 40 as well as the sealing lip 22 have a similar or identical shape.

As an alternative embodiment the fixing ring 30 may also have an inverted U-shaped upper portion so that it can be pushed over the projection 18 of the housing 10. In this case fixing elements may be provided on one or both of the legs of the U-shaped portion of the fixing ring 30.

In a further embodiment the fixing ring 30 and the projection 18 may have a thread or other suitable fixing elements.

Figure 4:
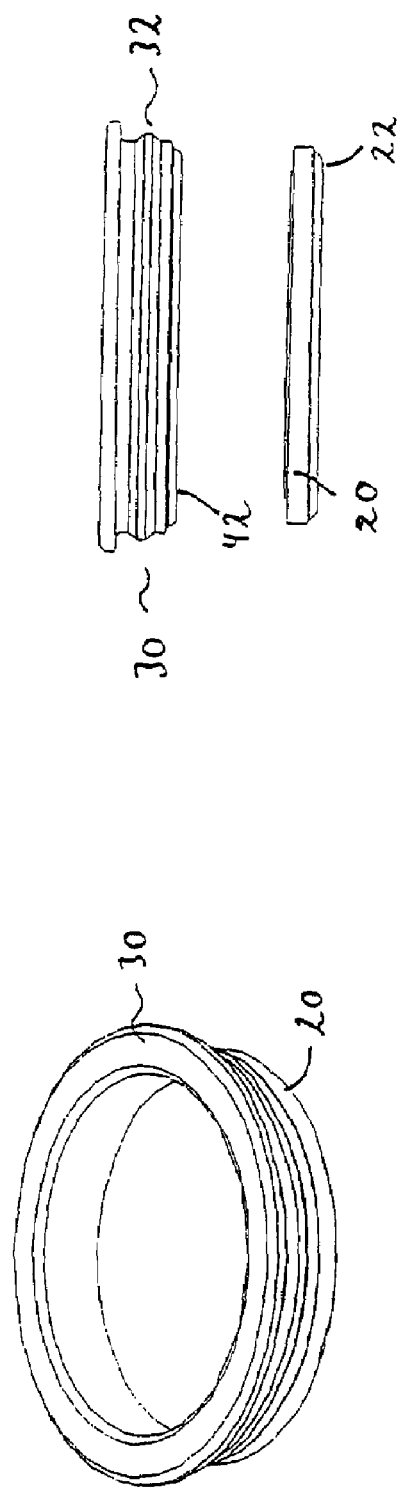

FIG. 4 shows different views of the membrane unit composed of membrane 20 and fixing ring 30. The embodiment of FIG. 4 corresponds to that shown in FIG. 3. As may be gathered from FIG. 4 the membrane unit is composed of two parts which are linked to each other after manufacture thereof for example by glueing or welding. After the assembly the complete unit consisting of membrane 20 and fixing ring 30 is inserted into the housing 10 shown in FIG. 1.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A membrane unit configured for use in a housing of a pressure measuring unit for measuring pressure of blood in an extra-corporeal blood circuit, comprising:
   a flexible membrane and a fixing ring which is integral with the membrane such that the membrane and the fixing ring form a one-piece element, the fixing ring having a lower flexibility than the membrane and the fixing ring including at least one fixing element for fixing the fixing ring to the housing,
   a contact surface between the membrane and the fixing ring being not flat and having at least one projection extending from at least one of the membrane and the fixing ring, the projection engaging with at least one groove in the other of the membrane and the fixing ring.

2. The membrane unit according to claim 1, wherein the fixing ring and the membrane are secured to each other.

3. The membrane unit according to claim 2, wherein the fixing ring and the membrane are secured to each other by at least one of gluing and welding.

4. The membrane unit according to claim 1, wherein the fixing ring and the membrane are configured as a joint manufacture from a common process of manufacture.

5. The membrane unit according to claim 4, wherein the fixing ring and the membrane are a two-component injection molded manufacture.

6. The membrane unit according to claim 1, wherein the at least one fixing element of the fixing ring is configured as at least one of a projection, a groove, and a thread.

7. The membrane unit according to claim 6, wherein the at least one fixing element of the fixing ring is located at an outside area of the fixing ring.

8. The membrane unit according to claim 7, wherein the fixing ring includes a U-shaped portion, and the fixing element is located on at least one of facing sides of legs of the U-shaped portion.

9. The membrane unit according to claim 1, wherein the fixing ring is joined perpendicular to the membrane.

10. The membrane unit according to claim 1, wherein the membrane has a circumferential portion and a central portion, the circumferential portion having a larger thickness than the central portion.

11. The membrane unit according to claim 10, wherein the sealing lip together with a larger thickness portion in the circumferential portion of the membrane extends into a first direction perpendicular relative to a planar area defined by the central portion of the membrane and the fixing ring extends relative to the planar area in a direction opposite to said first direction.

12. The membrane unit according to claim 1, wherein the membrane has a circumferentially extending sealing lip for sealing the contact surface between the membrane and said housing.

13. The membrane unit according to claim 12, wherein the sealing lip of the membrane has a shape that equals a shape of the contact surface between the membrane and the fixing ring.

14. The membrane unit according to claim 1, wherein the membrane has a groove on the surface facing the fixing ring.

15. A pressure measuring unit comprising a membrane unit according to claim 1, the fixing elements of the membrane unit engaging with the fixing elements of the housing and the membrane of the membrane unit forming one surface of the pressure measuring chamber of the housing.

16. A housing of a pressure measuring unit for measuring pressure of blood in an extra-corporeal blood circuit, comprising an inlet and an outlet for a fluid the pressure of which is to be measured and a pressure measuring chamber located in fluid communication with the inlet and the outlet, the pressure measuring chamber having an opening that is closable by a membrane inserted into the housing, the housing including fixing elements for fixing the membrane unit according to claim 1 to the housing with the fixing elements being located at at least one of the projections extending around said opening of the pressure measuring chamber.

17. The housing according to claim 16, wherein the projection extends perpendicularly relative to said opening of the pressure measuring chamber.

18. The housing according to claim 16, wherein the fixing elements of the projection are configured as at least one of a groove, a jut, and a thread.

19. The housing according to claim 16, wherein the fixing elements are located on a side of the projection which is oriented to said opening of the pressure measuring chamber.

20. A pressure measuring unit comprising a housing according to claim 16, the fixing elements of the membrane unit engaging with the fixing elements of the housing and the membrane of the membrane unit forming one surface of the pressure measuring chamber of the housing.

* * * * *